US007262797B2

(12) United States Patent
Weldum et al.

(10) Patent No.: US 7,262,797 B2
(45) Date of Patent: Aug. 28, 2007

(54) METHOD AND SYSTEM FOR STORING CALIBRATION DATA WITHIN IMAGE FILES

(75) Inventors: David L. Weldum, Jamesville, NY (US); Clark A. Bendall, Syracuse, NY (US); Michael C. Lesmerises, Liverpool, NY (US); Thomas W. Karpen, Skaneateles, NY (US); Jon R. Salvati, Skaneateles, NY (US)

(73) Assignee: GE Inspection Technologies LP, Lewiston, PA (US)

( * ) Notice: Subject to any disclaimer, the term of this patent is extended or adjusted under 35 U.S.C. 154(b) by 0 days.

(21) Appl. No.: 10/853,817

(22) Filed: May 25, 2004

(65) Prior Publication Data

US 2004/0215413 A1 Oct. 28, 2004

Related U.S. Application Data

(62) Division of application No. 10/080,144, filed on Feb. 21, 2002, now abandoned.

(60) Provisional application No. 60/270,967, filed on Feb. 22, 2001.

(51) Int. Cl.
*H04N 5/76* (2006.01)
(52) U.S. Cl. ............... 348/231.3; 348/231.99
(58) Field of Classification Search ............ 348/231.1, 348/231.2, 231.3, 231.4, 231.5, 231.6, 45, 348/65, 72
See application file for complete search history.

(56) References Cited

U.S. PATENT DOCUMENTS

| 5,070,401 | A |   | 12/1991 | Salvati et al. |
| 5,335,061 | A |   | 8/1994 | Yamamoto et al. |
| 5,696,850 | A | * | 12/1997 | Parulski et al. .......... 348/231.6 |
| 5,701,155 | A |   | 12/1997 | Wood et al. |
| 5,840,481 | A |   | 11/1998 | Johnston et al. |
| 5,883,610 | A | * | 3/1999 | Jeon ........................... 345/629 |
| 5,911,036 | A | * | 6/1999 | Wright et al. ................ 700/259 |
| 6,011,617 | A |   | 1/2000 | Naudet |
| 6,266,430 | B1 |   | 7/2001 | Rhoads |
| 6,310,647 | B1 | * | 10/2001 | Parulski et al. ......... 348/231.99 |

(Continued)

FOREIGN PATENT DOCUMENTS

JP 2001-275934 10/2001

OTHER PUBLICATIONS

U.S. Appl. No. 10/056,868, Bendall et al.

(Continued)

*Primary Examiner*—David Ometz
*Assistant Examiner*—Luong T. Nguyen
(74) *Attorney, Agent, or Firm*—Marjama & Bilinski LLP

(57) ABSTRACT

A system and method for storing, within an image transfer medium, an image and image-specific data associated with the image includes obtaining the image-specific data from a probe such as a borescope or endoscope, obtaining the corresponding image, choosing a specific image transfer medium, writing the image to the medium, and writing the image-specific data to a marker in the medium. In this manner, storing a combination of image data and one or more of system calibration data, overlay replacement data, and audio comment data in a single file of either a non-standard file format or a standard file format that does not explicitly support the inclusion of these data types is possible.

9 Claims, 4 Drawing Sheets

U.S. PATENT DOCUMENTS

| | | |
|---|---|---|
| 6,338,716 B1 | 1/2002 | Hossack et al. |
| 6,461,298 B1 * | 10/2002 | Fenster et al. .............. 600/437 |
| 6,511,418 B2 | 1/2003 | Shahidi et al. |
| 6,850,794 B2 * | 2/2005 | Shahidi ...................... 600/427 |
| 6,890,296 B2 | 5/2005 | Ogawa |
| 6,914,625 B1 * | 7/2005 | Anderson et al. ........ 348/231.2 |
| 2004/0019255 A1 | 1/2004 | Sakiyama |
| 2004/0183900 A1 | 9/2004 | Karpen et al. |
| 2005/0050707 A1 | 3/2005 | Scott et al. |
| 2005/0129108 A1 | 6/2005 | Bendall et al. |
| 2005/0162643 A1 | 7/2005 | Karpen |
| 2005/0165275 A1 | 7/2005 | Von Felten et al. |
| 2005/0168571 A1 | 8/2005 | Lia et al. |
| 2005/0281520 A1 | 12/2005 | Kehoskie et al. |

OTHER PUBLICATIONS

U.S. Appl. No. 10/936,373, Bendall et al.
U.S. Appl. No. 60/691,359, Bendall et al.
U.S. Appl. No. 60/692,966, Karpen.
U.S. Appl. No. 60/693,824, Krauter et al.
U.S. Appl. 60/729,153, Salvati et al.
U.S. Appl. No. 11/294,285, Weldum et al.
U.S. Appl. No. 60/773,095, Lia.

* cited by examiner

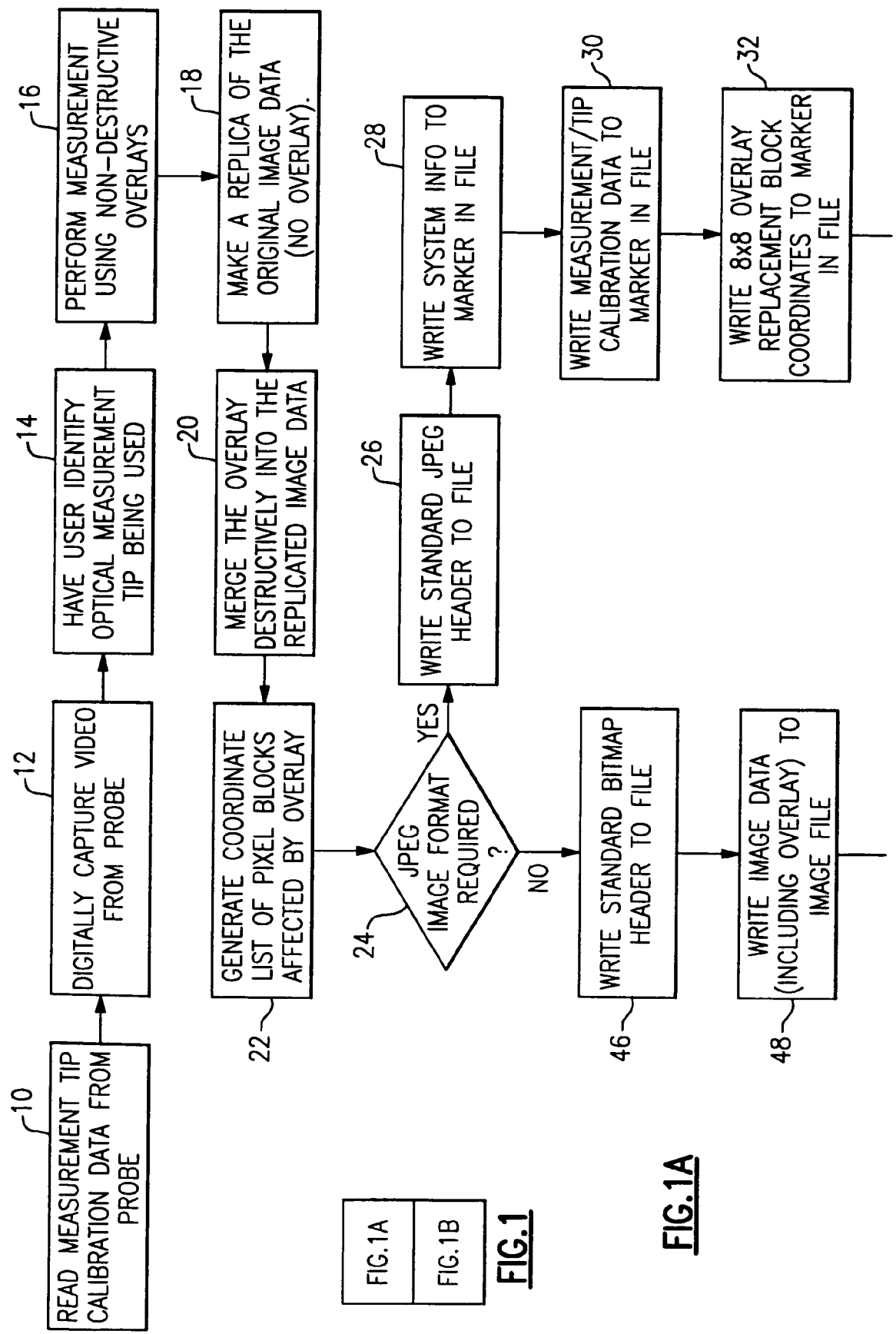

METHOD AND SYSTEM FOR STORING CALIBRATION DATA WITHIN IMAGE FILES

CROSS-REFERENCE TO RELATED APPLICATIONS

This application claims priority from U.S. Ser. No. 10/080,144 filed Feb. 21, 2002 now abandoned which claims priority from U.S. Provisional Application Ser. No. 60/270,967 filed Feb. 22, 2001 and entitled METHOD FOR STORING CALIBRATION DATA WITHIN IMAGE FILES, each of which are incorporated herein by reference.

FIELD OF THE INVENTION

This invention relates generally to the field of storing calibration data for a probe, and more particularly to a method for storing calibration data within image transfer media.

BACKGROUND OF THE INVENTION

In certain endoscopes/borescopes, hereinafter referred to as probes, there are data associated with the images, such as the calibration parameters for the measurement tip and probe that were used to capture the image, along with audio comments regarding the captured image, that must be kept with the images. In a competitive system, image data, audio data, and calibration data are each stored in separate files. This approach allows the audio and/or calibration data easily to become separated from the image making features such as off-line measurement and audio playback unusable. Embedding the data right in the image solves this problem.

Graphical overlay data added to images can obscure parts of the image. It is generally desirable for this overlay data to be viewable using standard software packages, but it is also desirable in some applications to be able to recover the image data that has been replaced by the overlay. This invention allows both goals to be met.

SUMMARY OF THE INVENTION

Briefly stated, a system and method for storing, within an image transfer medium, an image and image-specific data associated with the image includes obtaining the image-specific data from a probe such as a borescope or endoscope, obtaining the corresponding image, choosing a specific image transfer medium, writing the image to the medium, and writing the image-specific data to a marker in the medium. In this manner, storing a combination of image data and one or more of system calibration data, overlay replacement data, and audio comment data in a single file of either a non-standard file format or a standard file format that does not explicitly support the inclusion of these data types is possible.

According to an embodiment of the invention, a method for storing calibration data within image transfer media, includes the step of embedding data specific to a measurement system into the image transfer media so that the data is retrievable by a custom application directly from the image transfer media, thereby allowing re-measurement without using a second transfer media for measurement system information.

According to an embodiment of the invention, a method for storing overlay replacement data within image transfer media includes the step of embedding data into the image transfer media so that a destructive overlay added to the image is visible using a standard image viewer, and image data that was replaced by the destructive overlay is reconstituted from the embedded data.

According to an embodiment of the invention, a method for storing audio data along with an image within a standard image transfer media which does not provide explicit support for storing audio data includes the step of writing the audio data to a marker in the image transfer media such that the image is visible using a standard image viewer, while the audio data is retrievable by a custom application.

According to an embodiment of the invention, a method for storing image data and corresponding image-specific data includes the step of storing a combination of image data and one or more of system calibration data, overlay replacement data, and audio comment data in a single file of either a non-standard file format or a standard file format that does not explicitly support the inclusion of these data types.

According to an embodiment of the invention, a method for storing, within an image transfer medium, an image and image-specific data associated with the image includes the steps of obtaining the image-specific data; obtaining the image; choosing a specific image transfer medium; writing the image to the medium; and writing the image-specific data to a marker in the medium.

According to an embodiment of the invention, a system for storing calibration data within image transfer media includes means for embedding data specific to a measurement system into the image transfer media so that the data is retrievable by a custom application directly from the image transfer media, thereby allowing re-measurement without using a second transfer media for measurement system information.

According to an embodiment of the invention, a system for storing overlay replacement data within image transfer media includes means for embedding data into the image transfer media so that a destructive overlay added to the image is visible using a standard image viewer, and image data that was replaced by the destructive overlay is reconstituted from the embedded data.

According to an embodiment of the invention, a system for storing audio data along with an image within a standard image transfer media which does not provide explicit support for storing audio data includes means for writing the audio data to a marker in the image transfer media such that the image is visible using a standard image viewer, while the audio data is retrievable by a custom application.

According to an embodiment of the invention, a system for storing image data and corresponding image-specific data includes storing a combination of image data and one or more of system calibration data, overlay replacement data, and audio comment data in a single file of either a non-standard file format or a standard file format that does not explicitly support the inclusion of these data types.

According to an embodiment of the invention, a system for storing, within an image transfer medium, an image and image-specific data associated with the image includes means for obtaining the image-specific data; means for obtaining the image; means for choosing a specific image transfer medium; means for writing the image to the medium; and means for writing the image-specific data to a marker in the medium.

DETAILED DESCRIPTION OF THE PREFERRED EMBODIMENT

The method of the invention could be used in any system where there is a graphic overlay added to images that must be removable, or where there are non-graphical data related to an image that are required for later use with the image. In one application, the method is used to save shadow measurement tip calibration data and overlay removal data in bitmap and JPEG images captured using a videoprobe remote visual inspection system or an accompanying personal computer application. This allows images to have "destructive" overlays that are visible in the image using standard image viewing software, but which are removable by a custom application to present a clean image to the viewer. Storing tip calibration data in the image also allows measurements to be repeated on the image using either the system software or a custom PC-based software package. Similarly, audio data, such as comments, keywords, or phrases related to the image being viewed, could be included in the image file and later recovered. For example, if a person is inspecting the $5^{th}$ stage of engine type F110 serial number 123456, this information could be stored as audio data along with the image being viewed.

Figure 1B:
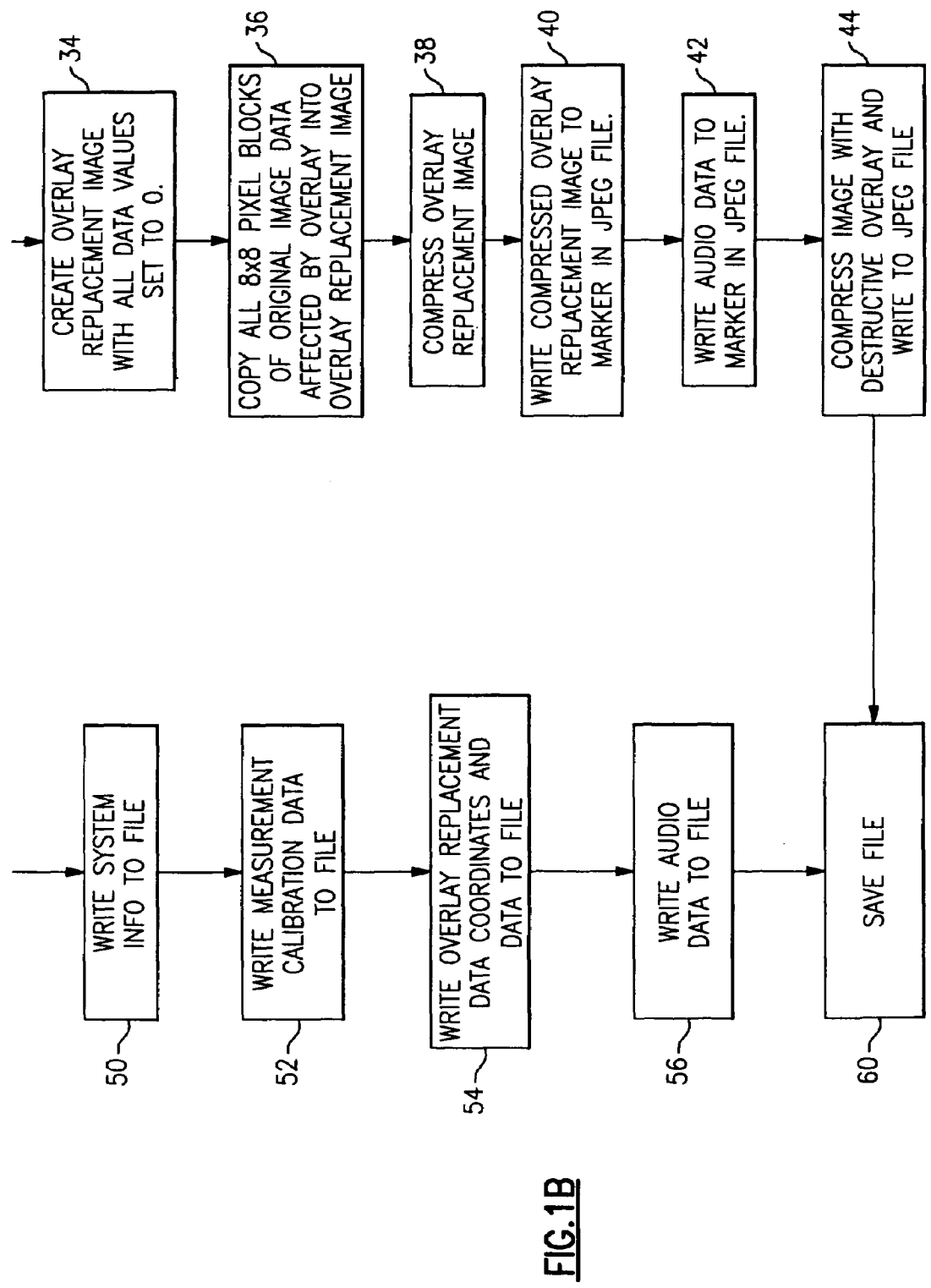
FIG. 1 shows the encoding process of the present invention.

Referring to FIG. 1, the encoding process of the invention is shown using calibration data for a borescope or endoscope (hereinafter referred to as a "probe") and a JPEG file as an example. In step 10, measurement tip calibration data is read. In step 12, the video image from the probe is captured. In step 14, the user identifies the specific optical measurement tip being used. The desired measurement, such as, for example, measuring the length of a defect observed with the probe, is performed using non-destructive overlays in step 16. A replica of the original image data with no overlay is made in step 18. Then, in step 20, the overlay is merged destructively into the replicated image data. In step 22, a coordinate list of pixel blocks affected by the overlay is generated.

In step 24 the question is asked whether or not JPEG image format is required, or whether bitmap format would work. If JPEG format is required, the standard JPEG header is written to the file in step 26. The JPEG file format allows for user-defined markers to be placed in the file. Each marker can specify up to 64 kilobytes of user data to follow. The markers and data are ignored by general image viewers, but can be read by application specific viewers. An embodiment of the invention places shadow measurement tip calibration parameters in one of these fields, and overlay replacement data in two or more others. Specifically, one marker stores a list of the coordinates of the 8×8 pixel-blocks in the image that contain overlay data. Another marker stores a compressed version of those 8×8 pixel-blocks without the overlay. If more than 64 kilobytes are required, additional markers are used. When the image is retrieved, these markers and data can be extracted, and the stored 8×8 pixel-blocks can be decompressed. They can then replace the corresponding pixel-blocks in the decompressed original image, effectively removing the overlay from the image. Additional markers could also be used to store audio data.

The system information is written to the marker in the file in step 28, after which the measurement/tip calibration data are written to the marker in the file in step 30. 8×8 overlay replacement block coordinates are written to the marker in the file in step 32. Then an overlay replacement image with all the data values set to zero is created in step 34. All 8×8 pixel blocks of original image data affected by the overlay are copied into the overlay replacement image in step 36. The overlay image is compressed in step 38, and then written to the marker in the JPEG file in step 40. In step 42, audio data is optionally written to the marker in the file if present. In step 44, the image with the destructive overlay is compressed and written to the JPEG file, after which the file is saved in step 60.

If JPEG format is not required, the standard bitmap header is written to the file in step 46. With bitmap images, the shadow measurement tip calibration parameters, the 8×8 pixel-block coordinate list, and the non-compressed 8×8 pixel-blocks are stored at the end of the file, after the image data. Audio data could also be added to the end of the file. General image viewers ignore this additional data, but application specific viewers can look for it and extract it. When the image is retrieved, the stored 8×8 pixel-blocks can replace the corresponding pixel-blocks in the original image, effectively removing the overlay from the image.

In step 48, the image data, including the overlay, is written to the image file. The system information is written to the file in step 50. Then, the measurement calibration data are written to the file in step 52, after which the overlay replacement data coordinates and the data are written to the file in step 54. Audio data is optionally written to the file in step 56, after which the file is saved in step 60.

Figure 2:
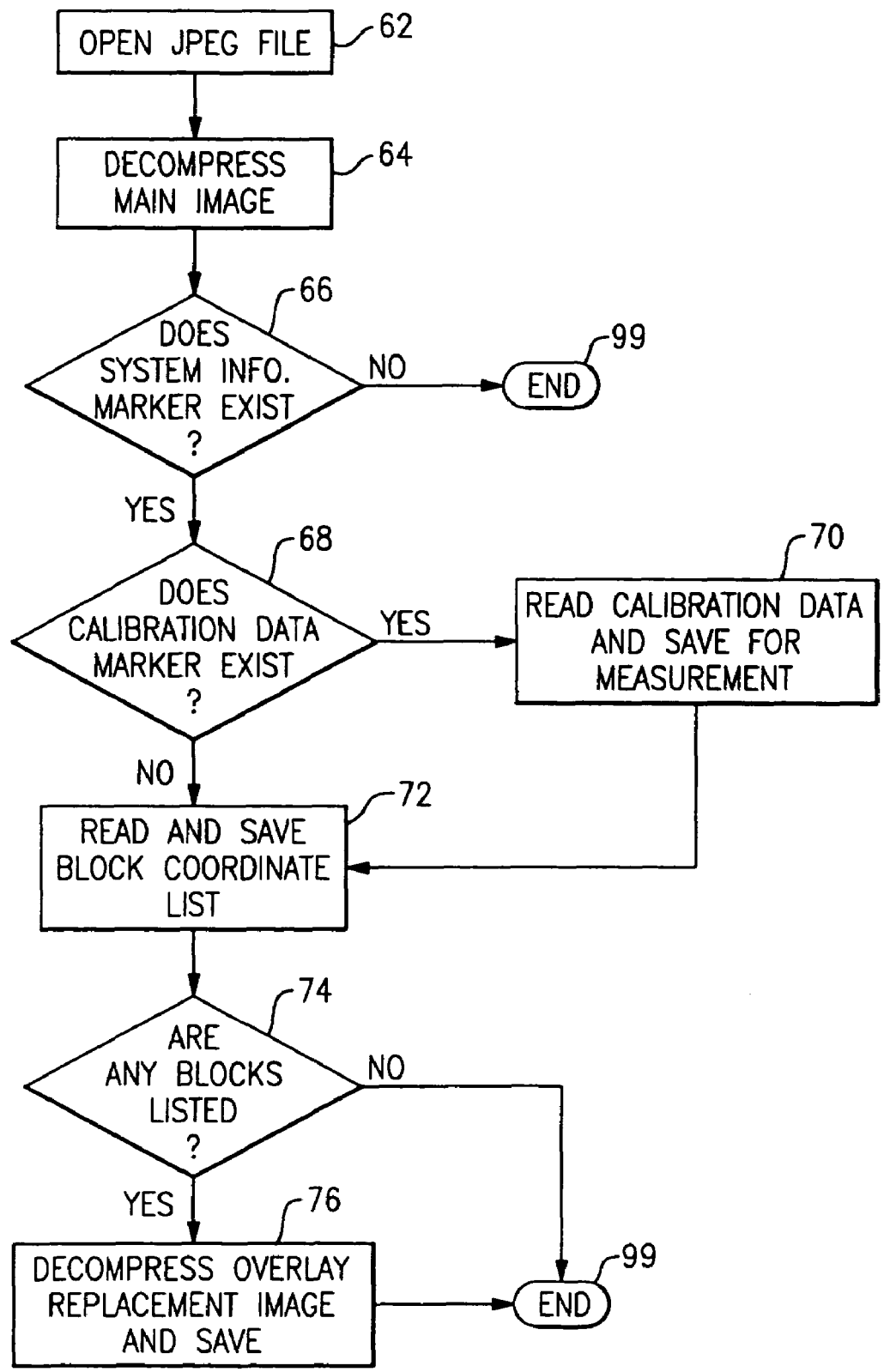
FIG. 2 shows the steps to recover data from a JPEG image file according to an embodiment of the invention.

Referring to FIG. 2, the steps to recover data from a JPEG image file are shown. The JPEG file is opened in step 62, after which the main image is decompressed in step 64. In step 66, the existence of the system information marker is checked. If the marker does not exist, the process ends in step 99. If the marker exists, the existence of the calibration data marker is checked in step 68. If the calibration data marker exists, the calibration data is read and saved for measurement in step 70. The block coordinate list is then read and saved in step 72. In step 74, the system checks to see if any blocks are listed, and if not, the process stops in step 99. Otherwise, the overlay replacement image is decompressed and saved.

Figure 3:
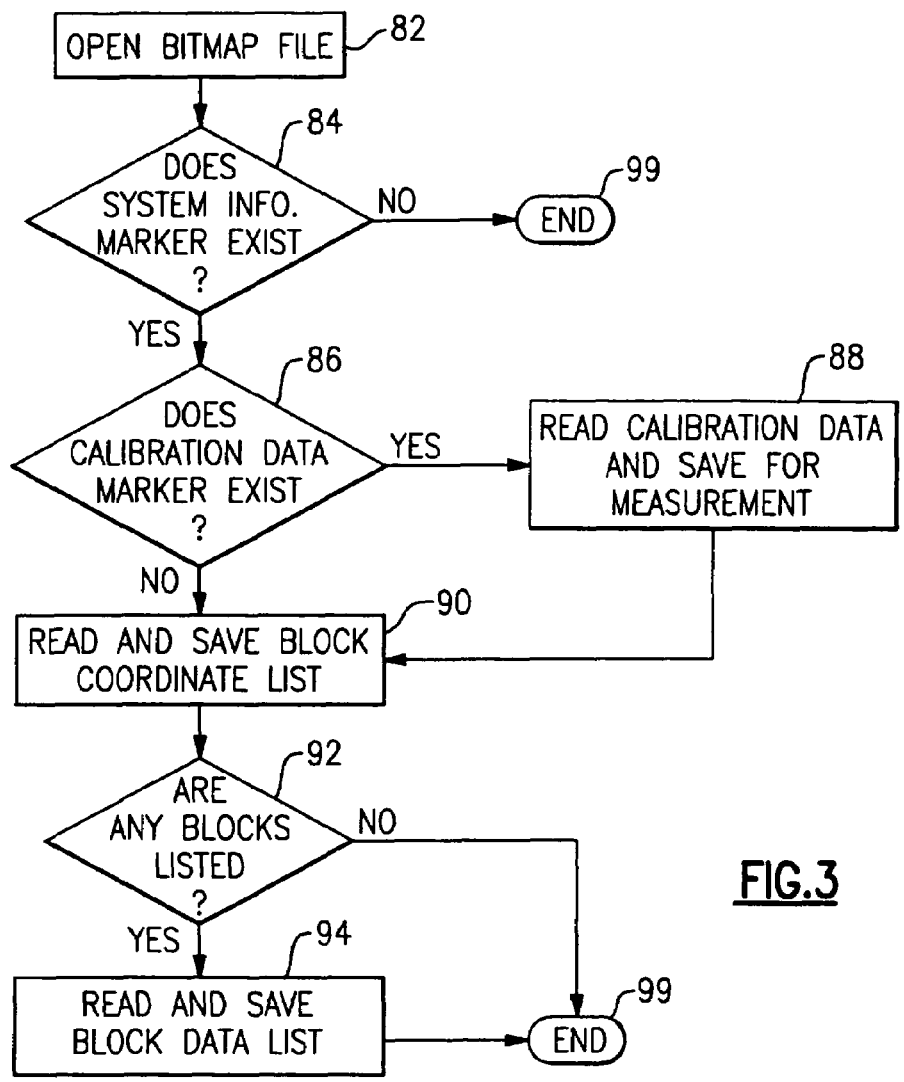
FIG. 3 shows the steps to recover data from a bitmap image file according to an embodiment of the invention.

Referring to FIG. 3, the steps to recover data from a bitmap file are shown. The bitmap file is opened in step 82, after which the existence of the system information marker is checked in step 84. If the system information marker is not present, the process ends at step 99. If the system information marker is present, the system looks for the calibration data marker in step 86. If the calibration data marker exists, the calibration data is read instep 88 and saved for measurement then the block coordinate list is read and saved in step 90. In step 92, the system checks to see if any blocks are listed. If no blocks are listed, the process ends at step 99. Otherwise, the block data list is read and saved in step 94.

Figure 4:
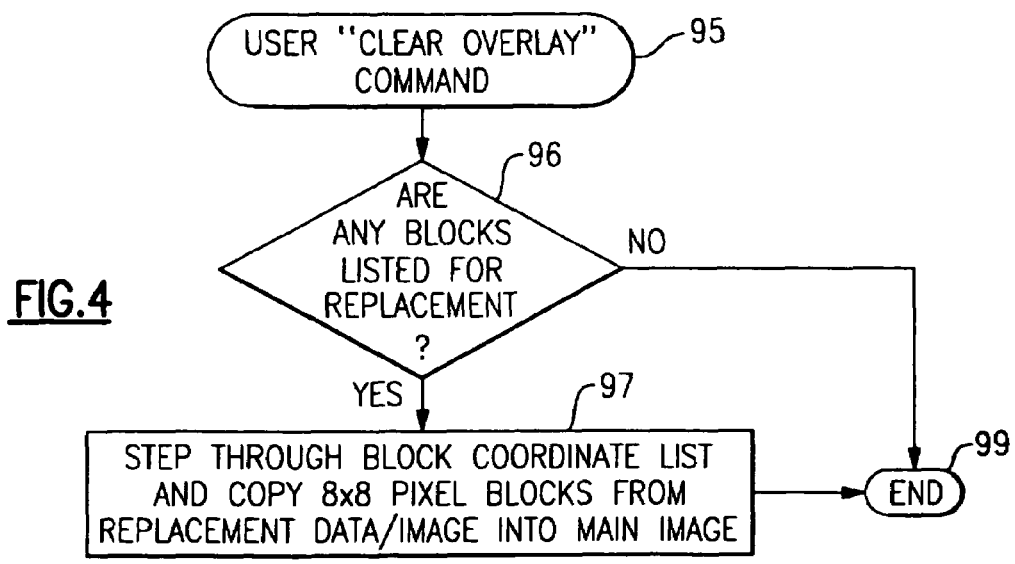
FIG. 4 shows the process the system uses to clear an overlay.

Referring to FIG. 4, the process the system uses to clear an overlay is shown. In step 95, the system checks to see if a user has issued a "clear overlay" command. If so, the system checks in step 96 to see if any blocks are listed for replacement. If not, the process ends at step 99. If any blocks are listed for replacement, in step 97 the block coordinate list is used to copy 8×8 pixel blocks from the replacement data/image into the main image.

There is a wide variety of image transfer media which can be used for the embedded measurement and overlay removal data. For example, the standard image transfer media can be digital still images such as JPEG, bitmap, TIFF, PCX etc.; digital motion video such as MPEG, AVI, etc.; and analog video using an approach similar to closed captioning. With the method of the present invention, the bitmap file structure preferably includes:
  (a) Bitmap Header,
  (b) Bitmap image data (with overlay),
  (c) System info section,
  (d) Measurement/tip calibration data section,
  (e) Overlay replacement coordinates/data, and
  (f) Audio comment data section.

The JPEG file structure preferably includes:
  (a) JPEG Header,
  (b) System info marker (JFIF Extension),
  (c) Measurement/tip calibration data marker (JFIF Extension),
  (d) Overlay replacement coordinates marker (JFIF Extension),
  (e) Compressed overlay replacement image marker (JFIF Extension),
  (f) Audio comment marker (JFIF Extension), and
  (g) Image data (with overlay).

The system info section/marker preferably includes:
  (a) Header to identify source and type of data,
  (b) Number of bytes in section,
  (c) Image dimensions,
  (d) Original image source, whether an endoscope system or not,
  (e) System software versions,
  (f) Standard optical distortion (for use in reference-based measurements),
  (g) System serial number,
  (h) Zoom level,
  (i) Image horizontally flipped from original or not,
  (j) Video standard of system (NTSC or PAL), and
  (k) Exposure control mode.

The measurement/tip calibration data section/marker preferably includes:
  (a) Header to identify source and type of data,
  (b) Number of bytes in section,
  (c) Positions of cursors from measurement screen,
  (d) Type of measurement performed,
  (e) Measurement result,
  (f) Format of tip calibration data,
  (g) Tip type (forward view or side view),
  (h) Tip color code,
  (i) Tip serial number,
  (j) Tip optical distortion,
  (k) Shadow geometry parameters, and
  (l) Checksum of tip calibration data.

The JPEG overlay replacement coordinates marker preferably includes:
  (a) Header to identify source and type of data,
  (b) Number of bytes in section, and
  (c) X/Y coordinates of 8×8 pixel blocks affected by overlay.

The JPEG overlay replacement data marker preferably includes:
  (a) Header to identify source and type of data,
  (b) Number of bytes in section, and
  (c) Compressed overlay replacement image where all 8×8 pixel blocks affected by overlay were filled with the original image data prior to compression. All blocks not affected by the overlay are set to values of 0 to allow maximum compression on those areas. JPEG compresses images in 8×8 pixel blocks. Information in one block does not affect the compression in any other block, so when the two compressed images are later uncompressed, the 8×8 blocks from the overlay replacement image used to "erase" the overlay are identical to what they would have been in the original image had there been no overlay.

The bitmap overlay data replacement section preferably includes:
  (a) Header to identify source and type of data,
  (b) Number of 8×8 pixel overlay replacement block packets in section, and
  (c) Series of block packets each consisting of horizontal and vertical block coordinates followed by 192 bytes of data (8×8 pixels per block, 1 red byte, 1 green byte, 1 blue byte per pixel).

The audio comment data marker/section preferably includes:
  (a) Header to identify source and type of data,
  (b) Number of bytes in section, and
  (c) Audio data.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

What is claimed is:

1. A method for storing overlay removal data within an image transfer media file, comprising the steps of:
    capturing an image from a videoprobe of a remote visual inspection system;
    generating a destructive overlay over said image captured from said videoprobe, thereby removing image data from said captured image;
    creating a first image transfer media file element representative of at least said image data removed from said captured image by said generated destructive overlay;
    creating a second image transfer media file element representative of said captured image and said generated destructive overlay; and
    embedding data from said first image transfer media file element and said second image transfer file element into said image transfer media file so that said captured image and said generated destructive overlay are visible using a standard image viewer, and said image data from said captured image that was removed by said generated destructive overlay can be reconstituted from said embedded data.

2. A method according to claim 1 further comprising the step of storing additional image-specific data within said image transfer media file by
    obtaining said image-specific data associated with said captured image from said videoprobe of the remote visual inspection system, a user of said remote visual inspection system, or both; and
    writing said image-specific data to a marker in said image transfer media file.

3. A method according to claim 2, wherein said image-specific data includes measurement tip calibration data from said videoprobe.

4. A method according to claim 2, wherein said image-specific data includes overlay replacement data associated with measurement.

5. A method according to claim 1, wherein said image transfer media file is one of a JPEG file, a bitmap file, and a TIFF file.

6. A method according to claim 1, further comprising the steps of:
  determining when a command is received to clear said generated destructive overlay from said captured image;
  retrieving information from said first image transfer media file element representative of at least said image data removed from said captured image by said generated destructive overlay; and
  replacing said generated destructive overlay with said information.

7. A method according to claim 2, further comprising the steps of: determining if said image-specific data is contained in said image transfer medium; and retrieving said image-specific data from said image transfer medium.

8. A method according to claim 7, wherein said image-specific data includes overlay replacement data associated with measurement.

9. A system for storing overlay removal data within an image transfer media file, comprising:
  means for capturing an image from a videoprobe of a remote visual inspection system;
  means for generating a destructive overlay over said image captured from said videoprobe, thereby removing image data from said captured image;
  means for creating a first image transfer media file element representative of at least said image data removed from said captured image by said generated destructive overlay;
  means for creating a second image transfer media file element representative of said captured image and said generated destructive overlay; and
  means for embedding data from said first image transfer media file element and said second image transfer file element into said image transfer media file so that said captured image and said generated destructive overlay are visible using a standard image viewer, and said image data that was removed by said generated destructive overlay can be reconstituted from said embedded data.

* * * * *